United States Patent [19]

Walleczek

[11] Patent Number: 5,383,023
[45] Date of Patent: Jan. 17, 1995

[54] METHOD AND APPARATUS FOR PERFORMING DUAL-BEAM DUAL-WAVELENGTH FLUORESCENCE SPECTROPHOTOMETRIC EVALUATION OF A BIOLOGICAL SPECIMEN

[76] Inventor: Jan Walleczek, 1318 Mills Ave., Redlands, Calif. 92373

[21] Appl. No.: 18,301

[22] Filed: Mar. 1, 1993

[51] Int. Cl.$^6$ ............................................. G01N 21/64
[52] U.S. Cl. .................................. 356/417; 356/317; 250/459.1
[58] Field of Search ............... 356/417, 320, 323, 325, 356/317, 318; 250/458.1, 459.1, 461.1, 461.2

[56] References Cited

U.S. PATENT DOCUMENTS

| | | | |
|---|---|---|---|
| 3,658,422 | 4/1972 | Wilkinson | 356/89 |
| 3,730,629 | 5/1973 | Rentzepis | 356/74 |
| 4,305,663 | 12/1981 | Perkins et al. | 356/323 |
| 4,320,970 | 3/1982 | Dowben et al. | 356/317 |
| 4,455,097 | 6/1984 | Ichikawa et al. | 356/323 |
| 4,484,815 | 11/1989 | Akiyama et al. | 356/325 |
| 4,795,256 | 1/1989 | Krause et al. | 356/320 |
| 4,849,362 | 7/1989 | DeMarinis et al. | 250/461.2 |
| 5,212,386 | 5/1993 | Gratton et al. | 356/317 |

OTHER PUBLICATIONS

Grynkiewicz et al., "A New Generation of $Ca^{+2}$ Indicators With Greatly Improved Fluorescence Properties", J. of Biological Chemistry, vol. 260, No. 6, Mar. 25, 1985, pp. 3440–3450.

Primary Examiner—Robert P. Limanek
Assistant Examiner—David B. Hardy
Attorney, Agent, or Firm—Hopgood, Calimafde, Kalil & Judlowe

[57] ABSTRACT

A quantitative fluorescence technique is presented as "differential real-time fluorescence spectroscopy" (DRFS), pursuant to which one can simultaneously make time-resolved measurement of fluorescence changes in two cuvette samples (e.g., experimental and control), wherein the fluorescence is induced by excitation light, and wherein both samples have been identically prepared with a selected ratiometric dye. The ratiometric dye may either be of excitation-shifted variety or of emission-shifted variety. With DRFS, it is possible to monitor the response of specimen cells to a chemical, biological or physical agent, in the absence and in the presence of a selected experimental variable, and to determine both of these responses in real time, i.e., at the same time as the measurements are being made. The invention is therefore ideally suited to monitor response from experimental stimuli that are expected to induce only relatively small cellular changes during the typical time course of a fluorescence measurement, namely, 20 minutes or less. The reason for this capability is that DRFS eliminates problems attributable to inherent biological variability associated with preparations of living cells, such as known and unknown (e.g., time-dependent) changes in base-line biological activity during the storage or handling of prepared cells, prior to and awaiting a particular experiment.

33 Claims, 5 Drawing Sheets

METHOD AND APPARATUS FOR PERFORMING DUAL-BEAM DUAL-WAVELENGTH FLUORESCENCE SPECTROPHOTOMETRIC EVALUATION OF A BIOLOGICAL SPECIMEN

BACKGROUND OF THE INVENTION

The invention relates to fluorescence spectrophotometric equipment and methods, particularly for making high-precision measurements in the determination of specimen response to a chemical, biological or physical agent wherein evaluation is made for a "control" sample of the specimen in relation to an "experimental" sample of the specimen.

U.S. Pat. Nos. 4,795,256 and 5,039,219 are illustrative of state-of-the-art precision fluorescence spectrophotometric equipment in which instrument sensitivity (e.g., as defined by signal/noise ratio) is high and cuvette-based fluorescence experiments are conventionally made, using one sample at a time. However, high-precision measurements do not necessarily yield meaningful and accurate results, particularly when one is concerned with the accuracy with which weak external influences on real-time kinetics of samples of biological cells are to be determined by fluorimetry. The accuracy of any experimental evaluation is limited by repeatability, that is, the extent to which a measurement with the same initial conditions (e.g., including the same biological state of the sample) will produce the same result. For example, when data from two or more consecutive fluorescence recordings (i.e., "experimental" and "control") are compared, it is generally assumed that the quantitative biological response patterns (i.e., kinetics) are the same. However, this may not always be the case, in that the false assumption of a constant cell response will be reflected in erroneously interpreted results. In other words, two separate recordings will differ, not because of imprecise measurements, but because the response kinetics may have changed in one or more significant ways. If a change in response kinetics is not accounted for, the change will factor into a measured fluorescence change, consequently prompting an inaccurate interpretation of results.

BRIEF STATEMENT OF THE INVENTION

It is an object of the invention to provide an improved method and apparatus for fluorescent spectroscopic examination of a specimen, wherein the above-noted inaccuracy can be eliminated or at least very substantially reduced.

It is a specific object to meet the above object with methodology whereby two or more samples of virtually identical biological response patterns can be analyzed simultaneously, whereby to achieve results that can be compared on a real-time basis.

Another specific object is to meet the above objects for the case of a dual-fluorescence analysis.

A further specific object is to provide an improved method and apparatus for fluorescent spectroscopic analysis whereby to achieve substantially greater accuracy and reproducibility of observations, particularly for cases in which the experimental specimen is subjected to a relatively weak chemical, biological or physical agent, such as a weak electromagnetic field.

It is also a specific object in a dual-beam dual-wavelength fluorescence system to make instrumental time resolution independent of any switching of light paths that may be involved in the measurement process.

A general object is to meet the above objects with apparatus which involves relatively little departure from what is commercially available, and which is inherently capable of performing a vastly greater number of experiments in a given time, as compared to prior techniques.

The invention in a preferred mode meets the above objects with what I believe to be a new quantitative fluorescence technique which I term differential real-time fluorescence spectroscopy (DRFS), pursuant to which one can simultaneously make time-resolved measurement of fluorescence changes in two cuvette samples (e.g., experimental and control), wherein the fluorescence is induced by excitation light, and wherein both samples have been identically prepared with a selected ratiometric dye. The ratiometric dye may either be of excitation-shifted variety or of emission-shifted variety. With DRFS, it is possible to monitor the response of specimen cells to a chemical, biological or physical agent, in the absence and in the presence of a selected experimental variable, and to determine both of these responses in real time, i.e., at the same time as the measurements are being made. The invention is therefore ideally suited to monitor response from experimental stimuli that are expected to induce only relatively small cellular changes during the typical time course of a fluorescence measurement, namely, 20 minutes or less. The reason for this capability is that DRFS eliminates problems attributable to inherent biological variability associated with preparations of living cells, such as known and unknown (e.g., time-dependent) changes in base-line biological activity during the storage or handling of prepared cells, prior to and awaiting a particular experiment.

By way of illustration, actual use of the invention will be described for an investigation of the dose-dependent acute effects of an inhibiting drug on stimulus-induced increases in intracellular calcium levels $[Ca^{2+}]_i$, in human leukemic T-lymphocyte cells.

DETAILED DESCRIPTION

Preferred and other embodiments of the invention will be described in detail, in conjunction with the accompanying drawings, in which.

Figure 1:
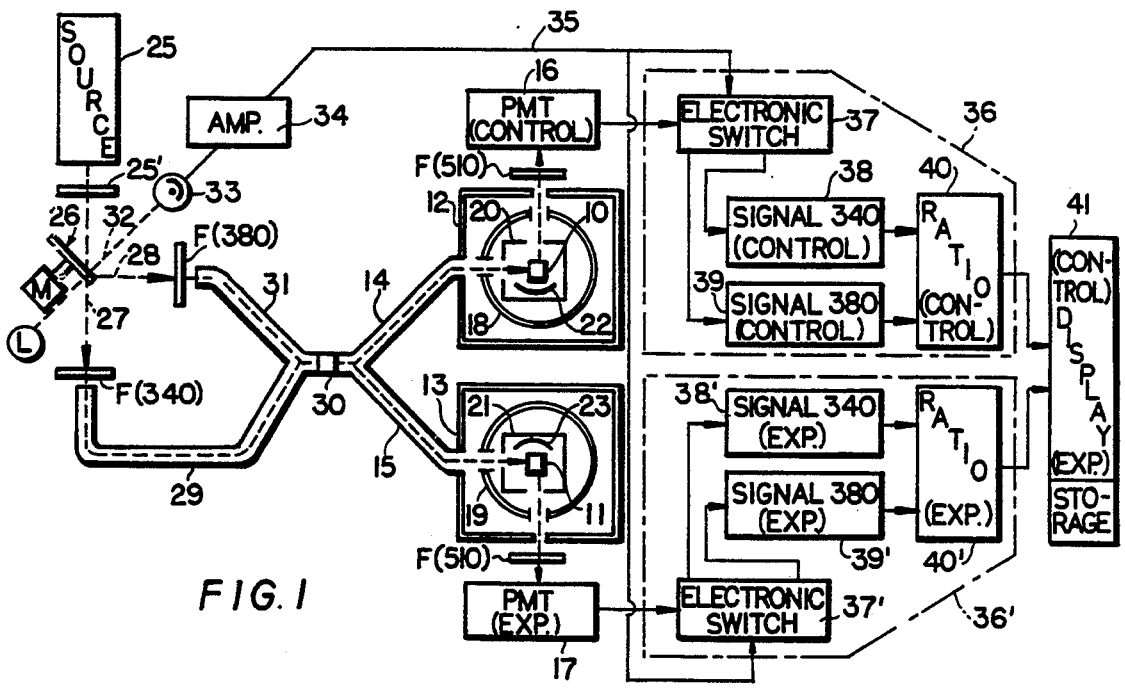
FIG. 1 is a diagram schematically showing optical and electrical components of a preferred embodiment of the invention, for the case of using an excitation-shifted ratiometric dye in dual-wavelength excitation measurements.

Referring initially to FIG. 1, the invention is shown as a dual-wavelength fluorescence spectrophotometric system for concurrently comparatively analyzing two identical specimens, respectively contained and supported in identical cuvettes 10, 11 in separate chambers 12, 13. Preparation of the specimens will be understood to have included a ratiometric fluorescent dye that will have been selected for the purposes of a particular experiment. In the present illustrative situation, changes in intracellular calcium concentration $[Ca^{2+}]_i$ will be assumed to be important to the experiment, and the dye Fura-2 will be assumed to have been selected for the purpose. Fura-2 is a well-known excitation-shifted dye suitable for detection of calcium; it is commercially available from Molecular Probes, Inc., Eugene, Oreg. Fura-2 is one of a variety of excitation-shifted dyes; it has the property of responding to excitation in one or both of two spaced relatively narrow bandwidths that are respectively centered at 340-nm and 380-nm, with fluorescence emission at 510-nm.

The chambers 12 (13) are identical, each having an inlet-porting alignment for exposing its cuvette 10 (11) to excitation light from an optical-fiber cable 14 (15), and an outlet-porting alignment for delivery of resultant fluorescent light to a photon detection device 16 (17) to measure fluorescent output. The designations PMT at 16 (17) will be understood to apply for devices which measure fluorescent output in the exiting beam from each of the respective chambers. Further symbolism within chambers 12 (13) will be understood illustratively to include identical coils 18 (19) for generating magnetic fields, identical thermostatically controlled cooling/heating systems 20 (21), and identical optical systems such as concave mirrors 22 (23) for more efficient direction of fluorescent-light output to the respective PMT's at 16 (17). In the labeling of the PMT's, parenthetical reference at 16 to "control" and at 17 to "EXP." (meaning "experimental") will be understood to designate the respective functional purposes of the identically prepared specimens at cuvettes 10, 11.

In accordance with an important feature of the invention, the lines 14, 15 of optical-fiber connection to chambers 12, 13 are identical and are supplied with like shares of light at 340-nm and at 380-nm, in equally shared time-interlaced relation. As shown, such light originates with a source 25, which may be a Xenon-arc lamp, producing an output beam on an optical axis to a continuously rotated mirror chopper 26, for splitting the lamp beam into two beams 27, 28, in equally shared time-interlaced alternation. The chopped and unreflected light of beam 27 is shown restricted by a first filter F(340) to the Fura-2 excitation-wavelength band, centered at 340-nm, for delivery of the same via a first optical-fiber cable 29 to an optical device 30; and the chopped and reflected light of beam 28 is restricted by a second filter F(380) to the second Fura-2 excitation-wavelength band, centered at 380-nm, for delivery of the same via a second optical-fiber cable 31 to the optical device 30. Cables 29, 31 are preferably of equal length and contain identical quantities of like optical fibers; cables 29, 31 may be the two branches of a single bifurcated fiber-optics bundled assembly. Similarly, the optical-fiber cables 14, 15 which deliver excitation light to the respective specimens 10, 11 may be the two branches of another and identical bifurcated fiber-optics bundled assembly, in turn assembled back-to-back at 30 with the assembly for cables 29, 31. The function at optical connection 30 is to assure in each of the cables 14, 15 an equally divided share of excitation light from each of the cables 29, 31. Description of items related to excitation light in FIG. 1 is completed by identifying a light beam 32 between a local source and a photocell 33, with interruption by chopper 26, whereby, with suitable amplification at 34, a signal is available in a synchronizing line 35, for purposes to be described. And a shutter 25' is suggested at the exit of light from source 25 to prevent incidence of excitation light on specimens at 10, 11, unless and until an experiment is being run.

The "control" PMT 16 will be seen to respond, for a specific calcium concentration, with a greater signal level for the chopped intervals of 340-nm exposure, in time-interlaced relation with a lesser signal level for the intervening chopped intervals of 380-nm exposure; in this connection, signal-to-noise at the excitation-shifted fluorescence wavelength 510-nm is enhanced by a suitable filter F(510). These PMT signals are then supplied to signal-processing means, collectively designated 36 for the "control" side of the system. Identical processing will be understood to exist for identical excitation on the "exp." side of the system, for which identical, duplicate signal-processing means is collectively designated 36'. The only difference between signals detected at PMT 16, as compared with those detected at PMT 17, is the fact of a selected one or more chemical, biological, or physical stimuli for the experimental-cuvette contents of chamber 13, as compared with the control-cuvette contents of chamber 12.

As shown, "control" signal-processing means 36 comprises an electronic switch 37 operating from the chopper-synchronizing signal in line 35. Switch 37 separates the time-interlaced signals, supplying to a first processing circuit 38 the segregated 510-nm fluorescent response to 340-nm excitation, and supplying to a second processing circuit 39 the segregated 510-nm fluorescent response to 380-nm excitation; suitably and preferably, the processing at 38, 39 includes analog/digital conversion, so that ensuing functions can be digitally processed. Output of the respective circuits 38, 39 is connected to a quotient-determining circuit 40, whereby the ratio of the signal which reflects response to 340-nm excitation, in relation to the signal which reflects response to 380-nm excitation is available for recording of the indicated "control" ratio, as a function of time in the on-going course of a given experiment. Identical signal-processing components for the "experimental" signals detected by PMT 17 need no further description and are therefore given the same reference numbers, with primed notation; the net result is that an "experimental"-signal ratio output from circuit 40' which also reflects response to 340-nm excitation, in relation to the signal which reflects response to 380-nm excitation, is available for recording of the indicated "experimental" ratio, as a function of the same time scale as the "control" ratio, in the same on-going course of the experiment. In FIG. 1, a single display means 41 is shown connected for simultaneous display and/or storage of involved "control" and "experimental" ratio determinations in real time.

Figure 2A:
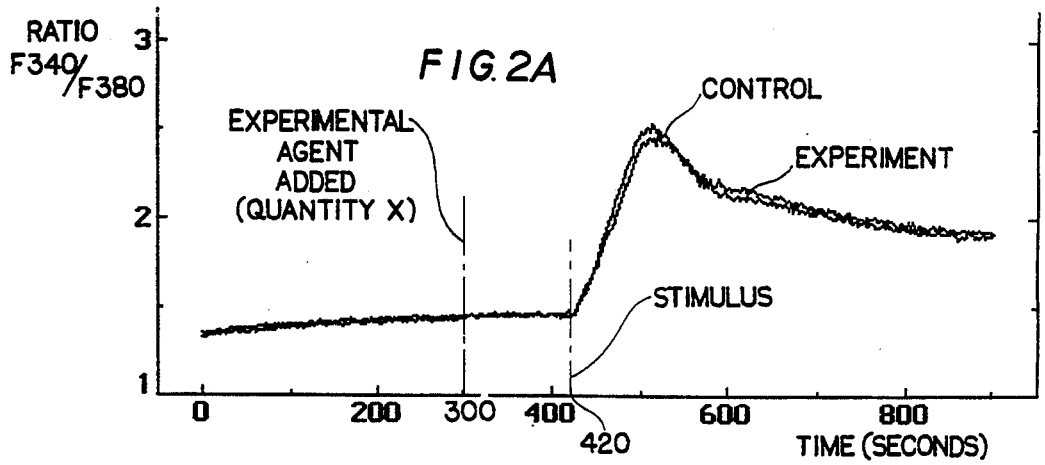
FIG. 2A is graphical recording made in use of the embodiment of FIG. 1, showing, in real time, measured fluorescence for identical "control" and "experimental" specimens as a function of the same time scale, and for the illustrative case of subjecting the experimental specimen to a relatively weak concentration of an inhibitory drug.
Figure 2B:
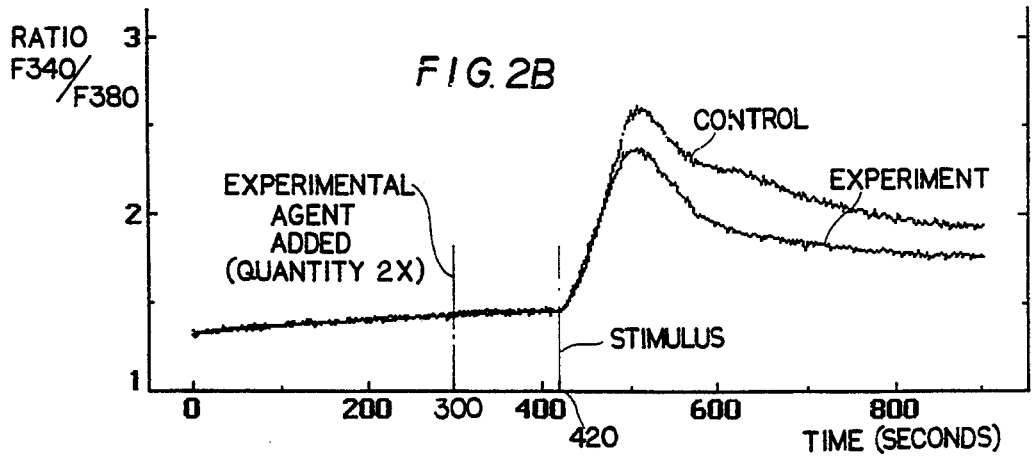
FIG. 2B is a recording similar to that of FIG. 2A, for case of a doubled concentration of the inhibitory drug.

FIGS. 2A and 2B are illustrative recordings made simultaneously and on a real-time basis, for a "control"

signal ratio (CTR) and an "experimental" signal ratio (EXP), wherein Fura-2 was the excitation-shifted dye used in the apparatus of FIG. 1, and wherein the traces shown in these FIGS. 2A and 2B are the raw-processed data available at the control/experimental display 41 of FIG. 1.

FIGS. 2A and 2B represent the time-evolution of the intracellular calcium concentration in Fura-2-loaded human leukemic T-lymphocyte cells (JURKAT-clone E6-1), wherein the displayed evolution proceeds in the time period 0 to 900 seconds, and wherein an increase in the ratio F340/F380 signifies an increase in intracellular calcium concentration in the T-lymphocyte cells, the same being suspended in a physiological buffer solution.

More specifically, in both FIGS. 2A and 2B, the time period 0 to 300 seconds reflects the base-line calcium levels in both the "experimental" and the "control" T-lymphocyte cell suspensions at cuvettes 10, 11, respectively. At time 300 seconds, a dose of a calcium-flux inhibitory drug, ECONAZOLE (0.25 $\mu$M in FIG. 2A, and 0.50 $\mu$M in FIG. 2B) was added, exclusively to the "experimental" cuvette sample 11; such doses will be observed not to lead to baseline deviations, as between the "experimental" and the "control" samples at 10 and 11. Then, at time 420 seconds, a "stimulus" applied equally to both the cell suspensions at 10, 11, was administered; the stimulus was "THAPSIGARGIN" at a concentration of 0.1 $\mu$M. This stimulus induced a rapid increase in intracellular calcium concentration in the involved cells, characterized by a peak at approximately 500 seconds, followed by a decline to essentially a plateau at about 900 seconds. FIGS. 2A and 2B illustrate the very noticeable difference in this peak attributable to the inhibitory drug, not only in the comparisons against the "control" response but also as a function of having doubled the drug concentration in the experiment of FIG. 2B. It is notable that even the influence of relatively weak drug administration on the stimulus-induced calcium-concentration rise (FIG. 2A) can be clearly discerned, by the dual-beam, dual-wavelength fluorescence spectrophotometric technique involved in a single experimental run with the apparatus of FIG. 1.

Figure 3:
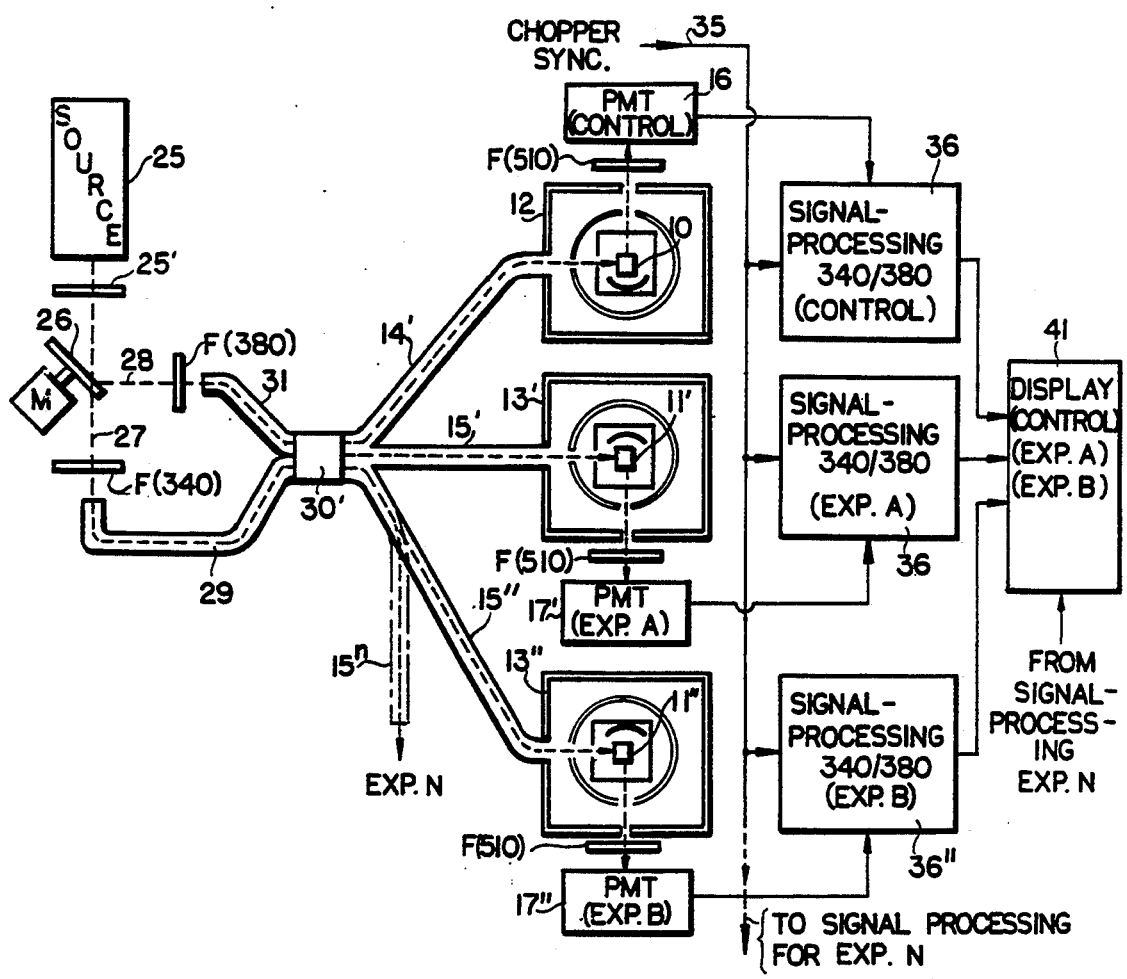
FIG. 3 is a diagram similar to FIG. 1, to illustrate application of the invention to real-time dual-wavelength fluorescence observation of a greater plurality of specimens.

The system of FIG. 3 will be seen as having great similarity to FIG. 1, with the exception that FIG. 3 illustrates that the invention is equally applicable to simultaneous real-time observation and measurement of plural specimens when the plurality exceeds two. The only limitation to the number of simultaneously observed specimens is that sufficient excitation-light flux shall be available from source 25, after spectral restriction to F(340) and F(380) distribution, with equally shared fractions of F(340) and F(380) light, divided at optical connection 30' into each of a plurality of optical-fiber cable branches 14', 15' and 15'', serving plural prepared specimens at cuvettes 10, 11' and 11'' in chambers 12, 13' and 13''. Legends at the single display means 41 indicate the capability of concurrently responding to the ratio output of signal-processing means 36 for the fluorescent output of the control specimen at 10, as well as (i) the ratio output of signal-processing means 36' for the fluorescent output of a first or Experiment-A specimen at 11', and (ii) the ratio output of signal-processing means 36'' for the fluorescent output of a second or Experiment-B specimen at 11''. In each of these three cases, the prepared specimens may illustratively have been identical, and the only difference in the course of a given run may, for example, be in the concentration of an added chemical agent, or the strength of an ambient electrical or magnetic field, as between Experiment A and Experiment B. A further reference numeral $15^n$ applied to a fragmentary phantom optical-fiber cable branch will be understood to indicate further equal sharing (at 30') of the time-interlaced dual-wavelength excitation light, to serve up to N experiments at a time, with processing identical to what has been described for Experiments A and B. And a legend applicable to an arrow in connection with display 41 is indicative of the fact that all processed experiments (A to N), plus the processed control signal can be presented comparatively, in real time and to the same time scale. As noted above, the limiting number of such further simultaneous experiments or measurements will depend upon whether the equal-sharing operation at 30' will deliver to each specimen sufficient light flux (at both of wavelengths 340-nm and 380-nm) to stimulate meaningful fluorescence at 510-nm (for each of the excitation wavelengths, 340-nm and 380-nm).

Figure 4:
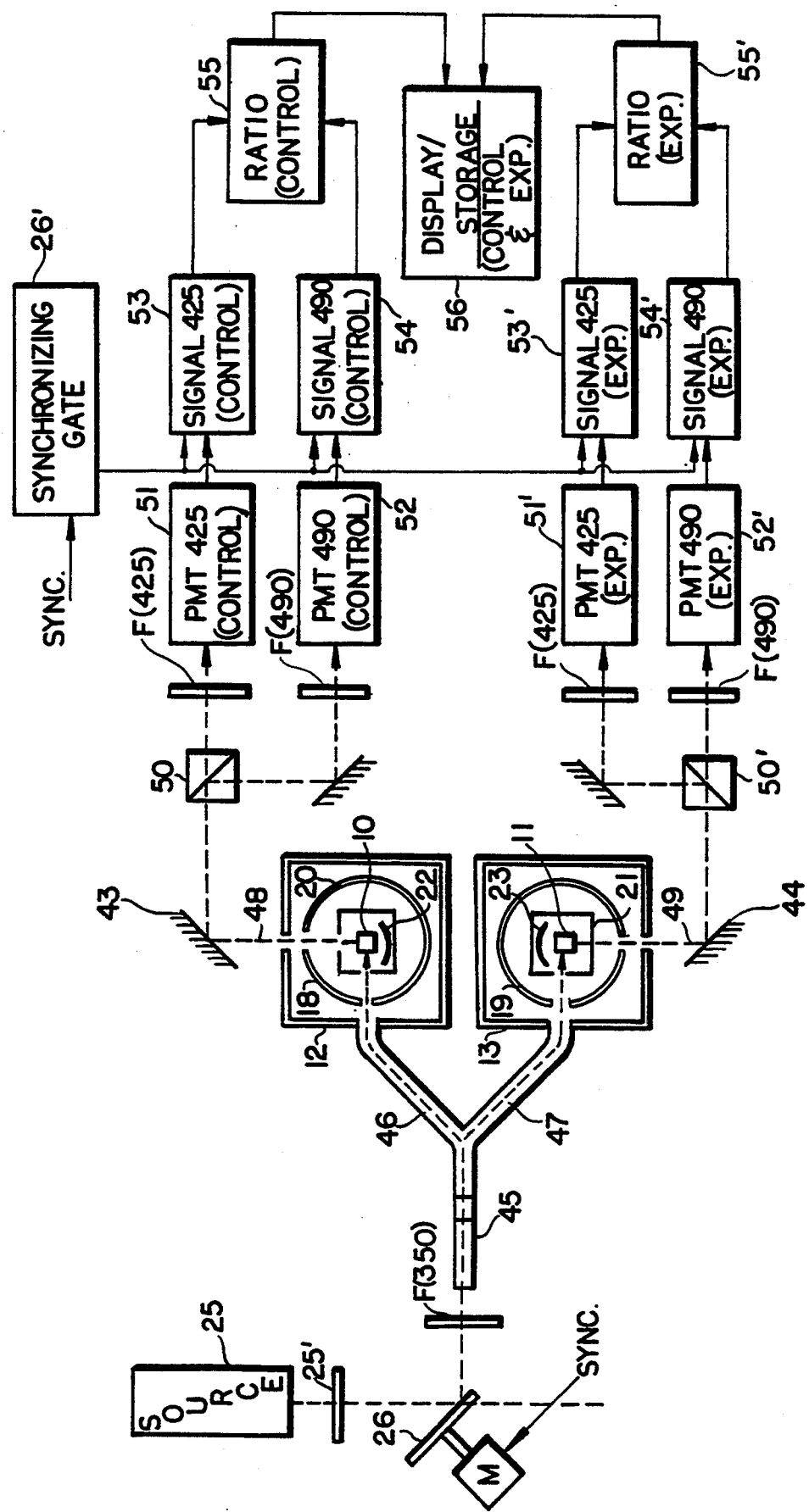
FIG. 4 is a diagram similar to FIG. 1 for another embodiment of the invention, for the case of using an emission-shifted ratiometric dye for dual-wavelength emission measurements.

The system of FIG. 4 illustrates use of the invention in a mode wherein dual-wavelength fluorescence results from use of an emission-shifted dye, which may be Indo-1, for observation of intracellular calcium $[Ca^{2+}]_i$ in a biological specimen. In an emission-shifted dye for dual-wavelength emission measurements, and for the case of Indo-1 in particular, a single narrow band of excitation light (centered at 350-nm) will develop fluorescent emission at two spaced narrow bands (centered at 425-nm and at 490-nm, respectively). Functional components in FIG. 4 therefore utilize these wavelength numbers for Indo-1 to designate functional relation to one or more of these wavelengths in a typical use of a ratiometric emission-shifted dye for dual-wavelength emission measurements, which in the case of FIG. 4 (as in FIG. 1) result in real-time development and display and/or storage of "control" and "experimental" ratio signals.

In the emission-shifted situation of FIG. 4, source 25 is required, in connection with a single filter F(350), to deliver only a single narrow band of excitation light to a single bifurcated optical-fiber bundle 45, with provision for equally shared delivery via branches 46, 47 to "control" and to "experimental" specimens at cuvettes 10, 11, within chambers 12, 13 as described in connection with FIG. 1. This may be done by direct and continuous delivery of light from source 25, via filter F(350), to the inlet end of the bifurcated fiber bundle 45; but in the form shown, preference is indicated that this delivery be made via chopper 26, with which other switching means as at 26', are synchronized, for signal-to-noise enhancement purposes; in FIG. 4, the legends "sync." applied at 26 and 26' will be understood to symbolize such synchronism.

In view of the dual-wavelength emission nature of Indo-1 dye used in specimens at 10, 11 in FIG. 4, the exiting fluorescent beams 48, 49 which issue from chambers 12 and 13 are each characterized by the two narrow bands centered at 425-nm and at 490-nm, respectively. Beams 48, 49 are shown folded at mirrors 43, 44 and split at 50, 50' into two spaced axes for narrow-band filtering at F(425) and at F(490), prior to separate measurement at 51 (PMT 425) and 52 (PMT 490) of "control" specimen fluorescence, and prior to separate measurement at 51' (PMT 425) and 52' (PMT 490) of "experimental" specimen fluorescence. Gate-26' controlled signal processing at 53, 54 of the respective PMT 425 and PMT 490 detected "Control" outputs at 51, 52 sets the stage for development at 55 of a ratio signal reflecting the instantaneous relative magnitude of "control" specimen fluorescence at the dual wavelengths attributable to use of Indo-1, and the ratio signal for the "control" specimen is supplied directly and continuously to display/storage means 56. Concurrently, gate-26' controlled signal processing at 53', 54' of the respective PMT 425 and PMT 490 detected "experimental" outputs at 51', 52' sets the stage for development at 55' of a ratio signal reflecting the instantaneous relative magnitude of "experimental" specimen fluorescence at the dual wavelengths attributable to use of Indo-1, and the ratio signal for the "experimental" specimen is supplied directly and continuously to display/storage means 56, for display with the "control" ratio signal and to the same time scale. The plotted display at 56 will be like that of FIGS. 2A and 2B, all other conditions being analogous, except for the fact of using an emission-shifted dye in FIG. 4, in place of an excitation-shifted dye in FIG. 1.

Figure 5:
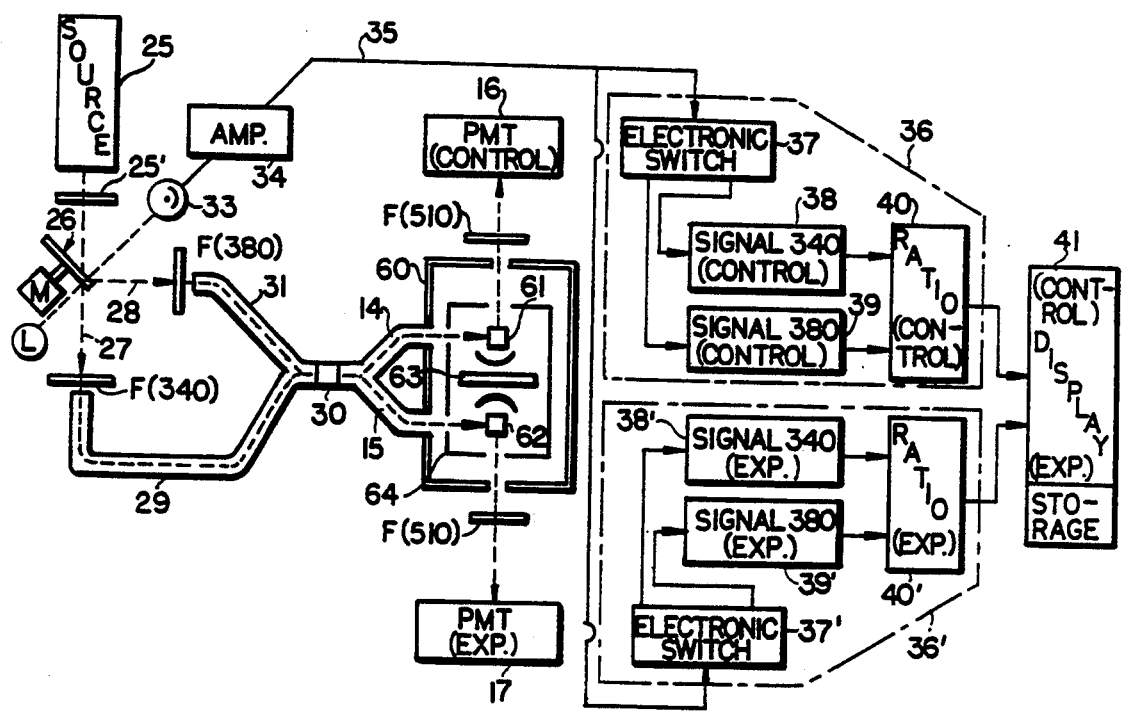
FIG. 5 is a diagram similar to FIG. 1 for a modification of FIG. 1, for making dual-wavelength excitation measurements using an excitation-shifted dye.

The system of FIG. 5 will be recognized for its correspondence to that of FIG. 1, except for use in FIG. 5 of a single chamber 60 to contain two identical cuvette specimens at 61, 62, for concurrent exposure to time-interlaced delivery of 340-nm excitation light in alternation with 380-nm excitation light, all as described for FIG. 1. For this reason, the same reference numbers are adopted in FIG. 5 as in FIG. 1 and no further separate discussion is needed, beyond pointing out that in chamber 60 of FIG. 5 there are two spaced inlet ports and two spaced outlet ports, with a light barrier 63 between cuvette specimens, for assurance against internally scattered "cross-talk" between "control" specimen fluorescence and "experimental" specimen fluorescence. Finally, the rectangular outline 64 around both cuvette specimens will be understood to indicate provision for thermostatically controlled uniform thermal environmental conditions for both specimens.

Figure 6:
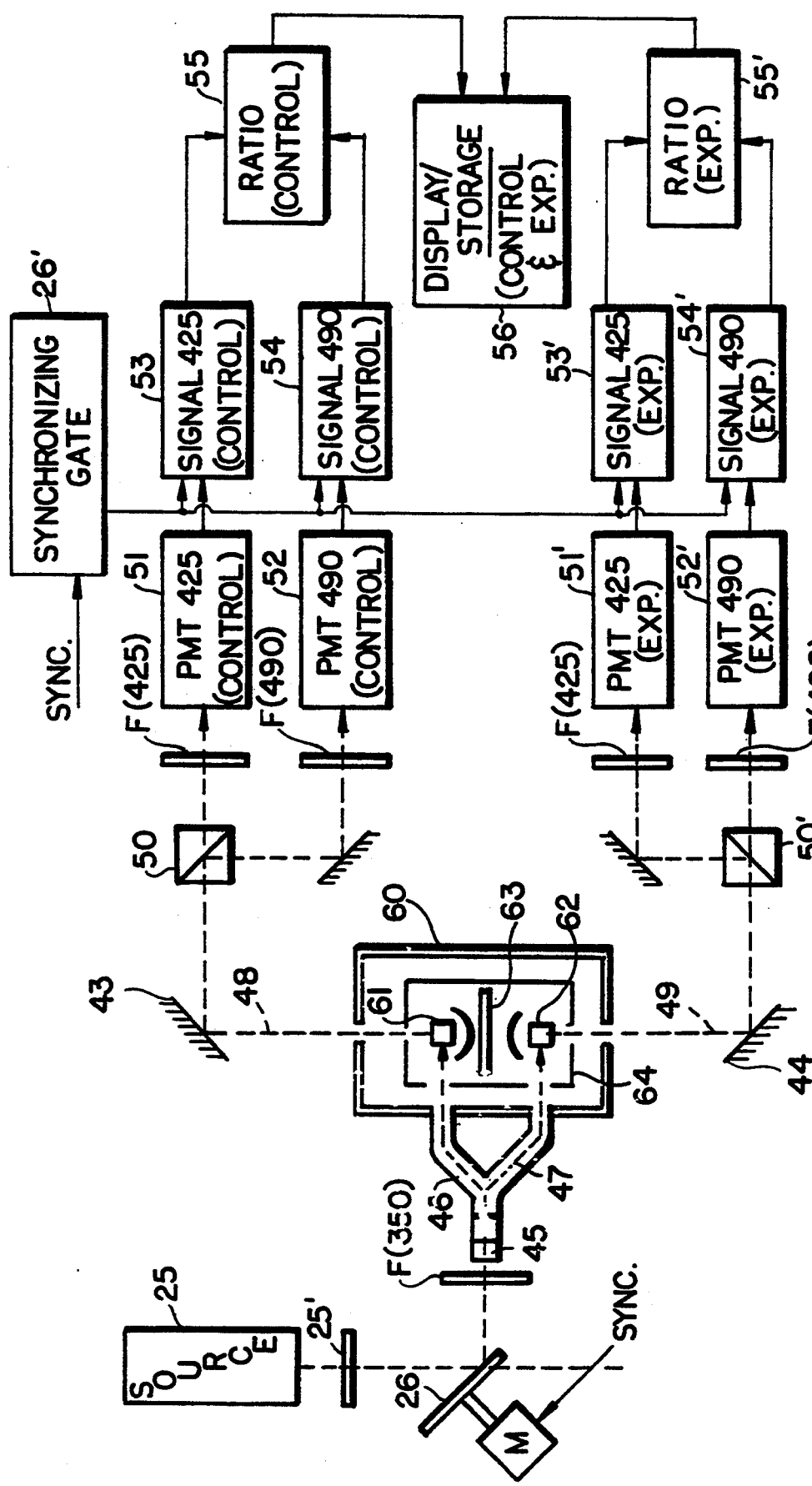
FIG. 6 is a diagram similar to FIG. 5 for a modification wherein dual-wavelength emission measurements are made using an emission-shifted ratiometric dye.

The system of FIG. 6 illustrates that the single chamber 60 of FIG. 5, containing plural cuvette specimens at 61, 62, is equally adaptable to use with an emission-shifted ratiometric dye (such as Indo-1) as such a single chamber was described in FIG. 5 for use with an excitation-shifted dye. This being the case, it is suitable in FIG. 6 to borrow from FIG. 4 most of the components described and shown in connection with involved emission-shifted fluorescence. Accordingly, where appropriate, the same reference numbers are used in FIG. 6 for components and functions as in FIG. 4, and further discussion is unnecessary.

It will be seen that the presently described techniques and apparatus meet the above-stated objects and provide substantial advantages over past and present techniques; these advantages include but are not limited to the following:

1. Problems associated with sequential measurements on a given specimen are eliminated by the simultaneous nature and real-time analysis provided by the invention.

2. The invention significantly reduces the time required for analysis of the effect of a given agent on a specific specimen, thus vastly improving efficiency of the measurement process.

3. For many applications, e.g., not involving magnetic-field experiments, the invention can be fully served by plural cuvette samples in a single chamber; and the use of separate chambers, i.e., one cuvette sample in each chamber, enables the efficient real-time analysis and measurement of the effect of a magnetic field on a given sample, in real-time comparison to a "control" sample which is not exposed to a magnetic field.

What is claimed is:

1. The method of performing a dual-wavelength fluorescence spectrophotometric evaluation of a specimen, which method comprises the steps of:
   (a) selecting a ratiometric fluorescent dye from the group comprising excitation-shifted dyes and emission-shifted dyes, wherein each of said dyes is identified with a first excitation-shifting light-exposure characteristic and with fluorescence at a second emission-shifted wavelength characteristic, and wherein one of said characteristics is specific to a single wavelength and the other of said characteristics is specific to two wavelengths;
   (b) preparing with the selected dye two identical cuvette samples of the specimen;
   (c) simultaneously exposing each of the prepared cuvette samples to equal fractions of light which accords with the first characteristic;
   (d) continuously and separately evaluating one cuvette sample for magnitude of fluorescent emission attributable to each of the two wavelengths of said other characteristic, whereby to enable development of a first ratio of fluorescent emissions from said one cuvette sample, and continuously generating a first electrical signal indicative of the ratio of one to the other of the separate evaluations of this step (d);
   (e) subjecting the other cuvette sample to a chemical, biological or physical agent;
   (f) continuously and separately evaluating the other cuvette sample for magnitude of fluorescent emission attributable to each of the two wavelengths of said other characteristic, whereby to enable development of a second ratio of fluorescent emissions from said second cuvette sample, and continuously generating a second electrical signal indicative of the ratio of one to the other of the separate evaluations of this step (f); and
   (g) concurrently utilizing the respective first and second electrical signals of steps (d) and (f) to a single time scale, wherein steps (c), (d) and (f) are performed currently.

2. The method of claim 1, in which step (g) comprises a concurrent display of the respective electrical signals to said single time scale.

3. The method of claim 1, in which the electrical signals of steps (d) and (f) are in digital format and step (g) includes entry of said signals into digital storage.

4. The method of claim 1, in which the selected dye is excitation-shifted and has a light-exposure characteristic consisting of two spaced wavelengths, and in which step (c) comprises simultaneously exposing each of the cuvette samples to time-interlaced light values wherein light of one of said two spaced wavelengths alternates with light of the other of said two spaced wavelengths.

5. The method of claim 1, in which the selected dye is emission-shifted and has a light-exposure characteristic consisting of a single wavelength, and in which step (c) comprises exposing each of the cuvette samples to light of said single wavelength, whereby fluorescent emission is at two spaced wavelengths; said method steps (d) and (f) each comprising filter separation of the respective two wavelengths of fluorescent emission for separate evaluation as the basis of generating the respective ratio signals.

6. The method of claim 1, in which steps (d) and (f) are performed concurrently.

7. The method of claim 1, in which after performing step (b) and before performing step (c), said one cuvette sample is subjected to a step (b'), namely, to a chemical, biological or physical agent which is different from the agent of step (e).

8. The method of claim 7, in which the agents of steps (b') and (e) are the same agent differing essentially only as to their relative strength or concentration.

9. The method of performing a dual-wavelength fluorescent spectrophotometric evaluation of specimen, using a source of time-interlaced light values wherein light of one wavelength alternates with light of another wavelength, said method comprising steps of:
 (a) preparing with a ratiometric fluorescent dye two identical cuvette samples of the specimen wherein said dye is an excitation-shifted dye selected for dual-excitation measurement to detect a particular ingredient or component of the specimen, whereby said dye is responsive to two spaced wavelengths of light which can excite the dye into fluorescence at a characteristic wavelength of fluorescent emission;
 (b) establishing said two spaced wavelengths as the respective wavelengths of said time-interlaced light values;
 (c) simultaneously exposing each of said cuvette samples to equal fractions of the time-interlaced light values;
 (d) synchronously evaluating, for one of said cuvette samples and for each of the time-interlaced light values of exposure, a separate fluorescence emission response at said fluorescence wavelength, whereby to enable development of a first ratio of fluorescent emission from said one cuvette sample, and generating an electrical signal indicative of the ratio of thus-sensed response;
 (e) subjecting the other cuvette sample to a chemical, biological or physical agent;
 (f) synchronously evaluating, for said other cuvette sample, and for each of the time-interlaced wavelengths of exposure, a separate fluorescence emission response at said fluorescence wavelength, whereby to enable development of a second ratio of fluorescent emission from said other cuvette sample, and generating an electrical signal indicative of the ratio of the thus-sensed responses of this step (f); and
 (g) concurrently displaying the respective electrical signals of steps (d) and (f) to a single time scale.

10. The method of claim 9, wherein step (e) is omitted for calibration purposes, whereby the display of step (g) will indicate any disparity as between the responses of the respective cuvette samples to the interlaced light values of source output, and
 (h) adjusting source-output exposure to one cuvette sample so as to reduce said disparity, before making the measurement involving step (d).

11. The method of performing a dual-wavelength fluorescent spectrophotometric evaluation of a biological specimen, using a source of light of essentially one wavelength, said method comprising the steps of:
 (a) preparing with a ratiometric fluorescent dye, two identical cuvette samples of the biological specimen, wherein said dye is an emission-shifted dye selected for dual-emission measurement to detect a particular ingredient or component of the specimen, whereby said dye is responsive to essentially a single wavelength of light by which it can be excited into fluorescence at two spaced characteristic wavelengths of fluorescent emission;
 (b) establishing said single wavelength as essentially said one wavelength;
 (c) simultaneously exposing each of said cuvette samples to equal fractions of the light of said one wavelength;
 (d) separately evaluating one cuvette sample for emitted fluorescent-light response at each of said two characteristic wavelengths, whereby to enable development of a first ratio of fluorescent-emission response at one with respect to the other of said characteristic wavelengths of fluorescent emissions, and developing an electrical signal indicative of the ratio of thus-sensed responses;
 (e) subjecting the other cuvette sample to a chemical, biological or physical agent;
 (f) separately evaluating said other cuvette sample for emitted fluorescent-light response at each of said two characteristic wavelengths, whereby to enable development of a second ratio of fluorescent-emission response at one with respect to the other of said characteristic wavelengths of fluorescent emission, and developing an electrical signal indicative of the ratio of thus-sensed responses; and
 (g) concurrently displaying the respective electrical signals of steps (c) and (e) to a single time scale.

12. The method of claim 11, wherein step (e) is omitted for calibration purposes, whereby the display of step (g) will indicate any disparity as between the responses of the respective cuvette samples to the light of said one wavelength, and
 (h) adjusting the level of said one-wavelength exposure to one cuvette sample so as to reduce said disparity, before making the measurement involving step (e).

13. The method of performing a dual-wavelength fluorescent spectrophotometric evaluation of a specimen, which method comprises the steps of:
 (a) selecting a ratiometric fluorescent dye from the group comprising excitation-shifted dyes and emission-shifted dyes, wherein each of said dyes is identified with a first excitation-shifting light-exposure characteristic and with fluorescence at a second emission-shifted wavelength characteristic, and wherein one of said characteristics is specific to a single wavelength and the other of said characteristics is specific to two wavelengths;
 (b) preparing with identical quantities of the selected dye two cuvette samples, each of which contains a different specimen;
 (c) simultaneously exposing each of the prepared cuvette samples to equal fractions of light which accords with the first characteristic;
 (d) continuously and separately evaluating one cuvette sample for magnitude of fluorescent emission attributable to each of the two wavelengths of said other characteristic, whereby to enable development of a first ratio of fluorescent-emission response for one with respect to the other of the wavelengths of said other characteristic, and continuously generating a first electrical signal indicative of the ratio of one to the other of the separate evaluations of this step (d);
 (e) subjecting both cuvette samples to the same chemical, biological or physical agent;

(f) continuously and separately evaluating the other cuvette sample for magnitude of fluorescent emission attributable to each of the two wavelengths of said other characteristic, whereby to enable development of a second ratio of fluorescent-emission response for one with respect to the other of the wavelengths of said other characteristic, and continuously generating a second electrical signal indicative of the ratio of one to the other of the separate evaluations of this step (f); and (g) concurrently utilizing the respective first and second electrical signals of steps (d) and (f) to a single time scale.

14. Apparatus for simultaneous measurement of fluorescent changes in two identical cuvette samples, each of which contains an equal quantity of a single ratiometric dye, wherein the measured changes are in response to exposure of one to the exclusion of the other of said samples to a chemical, biological or physical agent, said apparatus comprising:

(a) a dual-wavelength spectral source having an optical output in which light of one wavelength is in time-interlace with light of another wavelength;

(b) a first chamber for containing one of said cuvette samples and having a window through which said one sample can be exposed to at least a fraction of the time-interlaced output of said source, said first chamber including optical means and first photon-detection means responsive to a fluorescent wavelength of photons emitted by said one sample;

(c) a second chamber identical to said first chamber for containing the other of said cuvette samples, said second chamber additionally including means for subjecting said other cuvette sample to a chemical, biological or physical agent, whereby the photon-detection means of said second chamber will respond to said fluorescent wavelength for photons emitted by the agent-affected sample;

(d) optical means for concurrently delivering equally shared fractions of the time-interlaced output of said source to each of said chambers, whereby to enable for one of said chambers development of a first ratio of fluorescent-emission response to one with respect to the other of said shared fractions, and also concurrently to enable for the other of said chambers development of a second ratio of fluorescent-emission response to said one with respect to said other of said shared fractions;

(e) separate signal-processing means synchronized with the time-interlace of the output of said source for continuously developing (i) a first signal which is the ratio of first cuvette-sample response to the respective time-interlaced wavelengths, and (ii) a second signal which is the ratio of second cuvette-sample response to the respective time-interlaced wavelengths; and (f) utilization means responsive to said first and second signals for concurrently using said first and second signals as a function of a single time scale.

15. The apparatus of claim 14, in which said utilization means includes means displaying said signals in real time.

16. The apparatus of claim 14, in which said utilization means includes means for recording said signals in real time.

17. The apparatus of claim 14, in which said first and second signals are in digital form, and in which said utilization means includes means for digital storage of said first and second signals.

18. Apparatus for simultaneous measurement of fluorescent changes in two identical biological samples, in response to exposure of a single one of said samples to a chemical, biological or physical agent, said apparatus comprising:

(a) two identical cuvettes adapted for separate containment of the respective samples, wherein the samples are to include identical quantities of a selected excitation-shifted ratiometric dye which is characterized by responsivity to first and second wavelengths of light each of which will cause fluorescent emission at a single shifted emission wavelength;

(b) a dual-wavelength spectral source having an optical output in which light of one wavelength is in time-interlace with light of another wavelength, said source including means to select, for time-interlacing, the respective first and second wavelengths of a selected excitation-shifted ratiometric dye;

(c) a first chamber for containing one of said cuvette samples and having a window through which said one sample can be exposed to at least a fraction of the time-interlaced output of said source, said first chamber including optical means and first photon-detection means responsive to the emission wavelength of photons emitted by said one samplers;

(d) a second chamber identical to said first chamber for containing the other of said cuvette samples, said second chamber additionally including means for subjecting only said other cuvette sample to a chemical, biological or physical agent, whereby the photon-detection means of said second chamber will respond to said emission wavelength for photons emitted by the agent-exposed sample;

(e) optical means for concurrently delivering equally shared fractions of the time-interlaced output of said source to the sample in each of said chambers, whereby to enable for one of said chambers development of a first ratio of fluorescent-emission response to one with respect to the other of said shared fractions, and also concurrently to enable for the other of said chambers development of a second ratio of fluorescent-emission response to said one with respect to said other of said shared fractions;

(f) separate signal-processing means synchronized with the time-interlace of the output of said source for continuously developing (i) a first signal which is the ratio of first-sample response to the respective time-interlaced wavelengths, and (ii) a second signal which is the ratio of second-sample response to the respective time-interlaced wavelengths; and (g) display means responsive to said first and second signals for concurrently displaying said first and second signals as a function of a single time scale.

19. The apparatus of claim 18, in which said display means is a chart recorder wherein said first and second signals are displayed on a single grid of amplitude as a function of time.

20. The apparatus of claim 18, in which the separate signal-processing means produce their respective first and second output signals in digital form, and in which said display means includes means for entering into digital storage said first and second output signals.

21. The apparatus of claim 18, in which said optical means includes separate optical-fiber bundles having equally shared coupling to the time-interlaced output of said source, each of said bundles being coupled to one to the exclusion of the other of said chambers.

22. The apparatus of claim 18, in which said dual-wavelength spectral source comprises a lamp and shutter for selectively delivering light of spectral bandwidth which includes both said wavelengths, and means including a chopper and first and second narrowband filters for producing said optical output in time-interlace of said respective wavelengths.

23. The apparatus of claim 18, in which said second chamber further comprises a multi-turn coil of insulated electrical conductor surrounding the cuvette sample, and means to excite said coil whereby to establish a magnetic field as said physical agent.

24. Apparatus according to claim 18, in which said chambers, their cuvettes, their photon-detection means and associated signal-processing means are components of a chamber set and in which there are N chamber sets, wherein N is an integer equal to or greater than three; in which, the chambers of $N-1$ of said chamber sets are identical to said second chamber; and in which said optical means is adapted to delivering equally shared fractions of the time-interlaced output of said source to each of said chambers.

25. Apparatus for simultaneous measurement of fluorescent changes in two identical biological samples, in response to exposure of one to the exclusion of the other of said samples to a chemical, biological or physical agent, said apparatus comprising:
   (a) two identical cuvettes adapted for the separate containment of the respective samples, wherein the samples are to include identical quantities of a selected emission-shifted ratiometric dye which is characterized by responsitivity to essentially a single excitation wavelength of light which will cause fluorescence at each of two spaced and shifted emission wavelengths;
   (b) a single spectral source including means to select essentially said single wavelength for excitation of a selected emission-shifted ratiometric dye;
   (c) a first chamber for containing one of said cuvette samples and having a window through which said one sample can be exposed to at least a fraction of the single-wavelength output of said source, said first chamber including associated filter means and first and second photon-detection devices one of which is responsive to essentially only one of said emission wavelengths while the other photon-detection device is responsive to essentially only the other of said emission wavelengths;
   (d) a second chamber for containing the other of said cuvette samples and having a window through which said other sample can be exposed to at least a fraction of the single-wavelength output of said source, said second chamber including associated filter means and third and fourth photon-detection devices one of which is responsive to essentially only one of said emission wavelengths while the other of which is responsive to essentially only the other of said emission wavelengths;
   (e) optical means for delivering equally shared fractions of the essentially single wavelength of excitation light to the sample in each of said chambers, whereby to enable development, from said first chamber, of a first ratio of fluorescent-emission response to one with respect to the other of said shifted-emission wavelengths, an also to enable development, from said second chamber, of a second ratio of fluorescent-emission response to one with respect to the other of said shifted-emission wavelengths;
   (f) separate signal-processing means for continuously developing (i) a first signal which is the ratio of first-sample dual-wavelength fluorescence responses at the respective emission wavelengths, and (ii) a second signal which is the ratio of second-sample dual-wavelength fluorescence responses at the respective emission wavelengths; and
   (g) display means responsive to said first and second signals for concurrently displaying said first and second signals as a function of a single time scale.

26. Apparatus for simultaneous measurement of fluorescent changes in a plurality of identical cuvette samples, each containing an equal quantity of an excitation-shifted ratiometric dye, in response to exposure of all but one of said samples to a chemical, biological or physical agent, said apparatus comprising:
   (a) a dual-wavelength spectral source having an optical output in which light of essentially one wavelength is in time-interlace with light of essentially another wavelength, wherein said wavelengths are the respective excitation wavelengths of the dye;
   (b) a first chamber for containing one of said cuvette samples and having a window through which said one sample can be exposed to a fraction of the time-interlaced output of said source, said first chamber including optical means and a first photon-detection device responsive to a fluorescent wavelength of photons emitted by said one sample;
   (c) a further one or more chambers identical to said first chamber for respectively containing the other of said cuvette samples, each of said further chambers additionally including means for subjecting each of said other cuvette samples to a selected chemical, biological or physical agent, whereby the photon-detection device of each of said further chambers will respond to said fluorescent wavelength for photons emitted by a selected agent-subjected sample;
   (d) optical means for concurrently delivering equally shared fractions of the time-interlaced output of said source to each of said chambers, whereby to enable for one of said chambers development of a first ratio of fluorescent-emission response to one with respect to the other of said shared fractions, and also to concurrently enable for each of the other of said chambers independent development of its own uniquely determined ratio of fluorescent-emission response to said one with respect to said other of said shared fractions;
   (e) separate signal-processing means associated with each of said chambers and synchronized with the time-interlace of the output of said source for continuously developing for each of said chambers an independent signal which is the ratio of each-chamber response to light of the respective time-interlaced wavelengths; and
   (f) display means responsive to said independent signals for concurrently displaying a plurality of said independent signals as a function of a single time scale.

27. Apparatus for simultaneous measurement of fluorescent changes in a plurality of identical cuvette samples, in response to exposure of all but one of said samples to a chemical, biological or physical agent, wherein each of said samples contains an identical quantity of an emission-shifted ratiometric dye having a single excitation wavelength and two emission-shifted fluorescent wavelengths, said apparatus comprising:
- (a) a single-wavelength spectral source having an optical output of light of essentially the excitation wavelength of said dye;
- (b) a first chamber for containing one of said cuvette samples and having a window through which said one sample can be exposed to a fraction of the output of said source, said first chamber including optical means and a first two photon-detection devices separately responsive to the respective emission-shifted fluorescent wavelengths of photons emitted by said one sample;
- (c) a further one or more chambers identical to said first chamber for respectively containing the other of said cuvette samples, each of said further chambers additionally including means for subjecting each of said other cuvette samples to a selected chemical, biological or physical agent, whereby the two photon-detection devices of each said further chamber will respond to said fluorescent wavelengths for photons emitted by a selected agent-subjected sample;
- (d) optical means for concurrently delivering equally shared fractions of the output of said source to each of said chambers;
- (e) separate signal-processing means associated with each of said chambers for continuously developing for each of said chambers an independent ratio signal for each-chamber responses to the output of said source; and
- (f) display means responsive to said independent ratio signals for concurrently displaying a plurality of said independent ratio signals as a function of a single time scale.

28. Apparatus according to claim 27, in which the optical output of said single-wavelength source is a periodically chopped succession of light pulses of said single wavelength, and in which each of said separate signal-processing means includes a chop-synchronizing connection from said source.

29. Apparatus for simultaneous measurement of fluorescent changes in a plurality of identical cuvette samples, in response to exposure of single one of said samples to a chemical, biological or physical agent, wherein each of said samples contains an identical quantity of an excitation-shifted ratiometric dye having two excitation wavelengths and single emission-shifted fluorescent wavelength, said apparatus comprising:
- (a) a dual-wavelength spectral source having an optical output in which light of essentially one of said excitation wavelengths is in time-interlace with light of essentially the other of said excitation wavelengths;
- (b) a single chamber for containing said cuvette samples and having a window through which said samples can be exposed to at least a fraction of the time-interlaced output of said source, said single chamber including for each of said samples, optical means and a separate photon-detection device responsive to said emission-shifted fluorescent wavelength of photons emitted by each said sample;
- (c) optical means for concurrently delivering equally shared fractions of the time-interlaced output of said source to each of the cuvette samples in said chamber, whereby to enable for one of said cuvette samples development of a first ratio of fluorescent-emission response to light of one wavelength with respect to light of the other of said wavelengths, and also concurrently to enable for the other of said cuvette samples development of a second ratio of fluorescent-emission response to light of said one wavelength with respect to light of the other of said wavelengths;
- (d) separate signal-processing means coupled to each of said photon-detection devices and synchronized with the time-interlace of the output of said source for continuously developing for each of said samples an independent signal which is the ratio of each-sample response to the respective time-interlaced wavelengths; and
- (e) display means responsive to said independent signals for concurrently displaying a plurality of said independent signals as a function of a single time scale.

30. Apparatus for simultaneous measurement of fluorescent changes in a plurality of identical cuvette samples, in response to exposure of all but one of said samples to a chemical, biological or physical agent, wherein each of said samples contains an identical quantity of an emission-shifted ratiometric dye having a single excitation wavelength and two emission-shifted fluorescent wavelengths, said apparatus comprising:
- (a) a single-wavelength spectral source having an optical output of light of essentially the excitation wavelength of said dye;
- (b) a single chamber for containing said cuvette samples and having a window through which said samples can be exposed to a fraction of the output of said source, said single chamber including for each of said samples optical means and two photon-detection devices separately responsive to the emission-shifted fluorescent wavelengths of photons emitted by each said sample;
- (c) optical means for concurrently delivering equally shared fractions of the output of said source to each of the cuvette samples in said chamber;
- (d) additional means associated with the chambers of all but the chamber for said one sample for subjecting each of said all but one cuvette samples to a selected chemical, biological or physical agent;
- (e) separate signal-processing means coupled to each of said photon-detection devices for continuously developing for each of said cuvette samples an independent ratio signal for each-sample responses to the output of said source; and
- (f) display means responsive to said independent ratio signals for concurrently displaying a plurality of said independent ratio signals as a function of a single time scale.

31. A dual-beam, dual-wavelength fluorescence spectrophotometer for simultaneous measurement of fluorescent changes in two identical biological samples, each of which samples contains an equal quantity of a single excitation-shifted dye, and wherein the measured changes are in response to exposure of only one of said samples to a chemical, biological or physical agent, said apparatus comprising:
means for producing a dual-wavelength light beam, and for dividing said light beam into two equal shares on first and second optical paths, the two wavelengths of said beam being the respective excitation wavelengths of said dye;

a first cuvette containing one of said samples and positioned in one of said paths for exposure to one of said shares of said light beam;

a second cuvette containing the other of said samples and positioned in the other of said paths for exposure to the other share of said light beam;

means for subjecting said one cuvette sample to a chemical, biological or physical agent;

photon-detection means for continuously detecting fluorescent light emitted from the sample in each of said cuvettes and producing separate electrical-signal outputs for detected fluorescence emitted from the respective cuvette samples; and computer means for analyzing and simultaneously displaying in real-time the outputs from said photon-detection means.

32. Apparatus for simultaneous measurement of fluorescent changes in a plurality of identical cuvette samples in response to exposure of all but one of said samples to a chemical, biological or physical agent, wherein each of said samples contains an identical quantity of an excitation-shifted ratiometric dye having two excitation wavelengths and a single emission-shifted fluorescent wavelength, said apparatus comprising:

(a) a dual-wavelength spectral source having an optical output limited to each of the said excitation wavelengths of said dye;

(b) a first chamber for containing one of said cuvette samples and having a window through which said one sample can be exposed to a fraction of the output of said source, said first chamber including optical means and a first photon-detection device responsive to the said emission-shifted fluorescent wavelength of photons emitted by said one sample;

(c) a further one or more chambers identical to said first chamber for respectively containing the other of said cuvette samples, each of said further chambers additionally including means for subjecting each of said other cuvette samples to a selected chemical, biological or physical agent, whereby the photon-detection device of each said further chamber will respond to said fluorescent wavelength for photons emitted by a selected agent-subjected sample;

(d) optical means for concurrently delivering equally shared fractions of the output of said source to each of said chambers for continuously developing for each of said chambers an independent ratio signal for each-chamber response to the respective wavelengths of the output of said source; and (f) display means responsive to said independent ratio signals for concurrently displaying a plurality of said independent ratio signals as a function of a single time scale.

33. Apparatus for simultaneous measurement of fluorescent changes in a plurality of identical cuvette samples in response to exposure of all but one of said samples to a chemical, biological or physical agent, wherein each of said samples contains an identical quantity of an excitation-shifted ratiometric dye having two excitation wavelengths and a single emission-shifted fluorescent wavelength, said apparatus comprising:

(a) a dual-wavelength spectral source having an optical output limited to each of the said excitation wavelengths of said dye;

(b) a single chamber for containing said cuvette samples and having a window through which said one sample can be exposed to a fraction of the output of said source, said single chamber including for each of said samples, optical means and a photon-detection device separately responsive to the emission-shifted wavelength of photons emitted by said one sample;

(c) optical means for concurrently delivering equally shared fractions of the output of said source to each of the cuvette samples in said chamber;

(d) additional means associated with all but said one of said cuvette samples for subjecting each of said all but one cuvette samples to a selected chemical, biological or physical agent;

(e) separate signal-processing means coupled to each of said photon-detection devices for continuously developing for each of said cuvette samples an independent ratio signal for each-sample response to the respective wavelengths of the output of said source; and (f) display means responsive to said independent ratio signals for concurrently displaying a plurality of said independent ratio signals as a function of a single time scale.

* * * * *